US008691236B2

(12) United States Patent
Blalock et al.

(10) Patent No.: US 8,691,236 B2
(45) Date of Patent: Apr. 8, 2014

(54) VACCINE FOR A THERAPEUTIC OR A PROPHYLACTIC TREATMENT OF MYASTHENIA GRAVIS

(75) Inventors: J. Edwin Blalock, Vestavia Hills, AL (US); Stephane P. Huberty, Rixensart (BE)

(73) Assignee: Cura Vac, Inc., Wilmington, New Castle, DE (US)

( * ) Notice: Subject to any disclaimer, the term of this patent is extended or adjusted under 35 U.S.C. 154(b) by 797 days.

(21) Appl. No.: 12/294,109

(22) PCT Filed: Mar. 23, 2006

(86) PCT No.: PCT/US2006/010896
§ 371 (c)(1),
(2), (4) Date: Jan. 8, 2009

(87) PCT Pub. No.: WO2007/108808
PCT Pub. Date: Sep. 27, 2007

(65) Prior Publication Data
US 2009/0117138 A1    May 7, 2009

(51) Int. Cl.
*A61K 39/00* (2006.01)
*A61K 38/00* (2006.01)
(52) U.S. Cl.
USPC ........................................ 424/185.1; 530/326
(58) Field of Classification Search
None
See application file for complete search history.

(56) References Cited

FOREIGN PATENT DOCUMENTS

WO    WO00/69461    11/2000

OTHER PUBLICATIONS

Araga et al.,"Prevention of experimental autoimmune myasthenia gravis by manipulation of the immune network with a complementary peptide for the acetylcholine receptor," Proc. Natl. Acad. Sci., 1993, pp. 8747-8751, vol. 90.

Araga et al.,"A peptide vaccine that prevents experimental autoimmune myasthenis gravis by specifically blocking T cell help," FASEB J., 2000, pp. 185-196, vol. 14.
Mcanally et al.,"The role of adjuvants in the efficacy of a peptide vaccine for myasthenia gravis," Exp. Biol. Med., 2001, pp. 307-311, vol. 226, No. 4.
Araga, et al. Abstract only, Abstract No. P09.01, "Monoclonal Antibody (MAB) to a Complementary Peptide for Torpredo Aceylcholine Receptor (ACHR) Residues61-76 recognizes Idiotype Antibodies (ID-ABS): Possible Utility in Myasthenia Gravis (MG)", *Journal of Neuroimmunology*, vol. 54, No. 1-2, p. 150, Oct. 1994.
Araga, et al., "Prevention of Experimental Autoimmune Myasthenia Gravis by a Monoclonal Antibody to a Complementary Peptide for the Main Immunogenic Region of the Acetylcholine Receptor", *Journal of Immunology*, vol. 157, pp. 386-392, 1996.
Araga, et al., "Use of Complementary Peptides and Their Antibodies in B-Cell-Mediated Autoimmune Disease: Prevention of Experimental Autoimmune Myasthenia Gravis with a Peptide Vaccine", *Immunomethods*, vol. 5, pp. 130-135, 1994.
Galin, at al., "Possible therapeutic vaccine for canine myasthenia gravis: Implications for the human disease and associated fatigue", *Brain, Behavior, and Immunity*, vol. 21, pp. 323-331, 2007.
Shah, et al., "Alkylation of Tryptophan During Deprotection of Tmob-Protected Carboxamide Side Chains", *Peptide Research*, vol. 5, No. 4, pp. 241-244, 1992.
Weathington, et al., "Rational design of peptide vaccines for autoimmune disease: harnessing molecular recognition to fix a broken network", *Expert Review of Vaccine*, vol. 2(1), pp. 61-73, 2003.
Xu, et al., "Prevention and Reversal of Experimental Autoimmune Myasthenia Gravis by a Monoclonal Antibody against Acetylcholine Receptor-Specific T Cells", *Cellular Immunology*, vol. 208, pp. 107-114 2001.

*Primary Examiner* — Gerald R Ewoldt
(74) *Attorney, Agent, or Firm* — Browdy and Neimark, PLLC

(57) ABSTRACT

Complementary peptide having at least a sequence complementary to a major immunogenic region of an acetylcholine receptor involved in myasthenia gravis, characterized in that the complementary peptide has at least a sequence SEQ. ID. NO1 with a tryptophan in position 8, carrying at least one optionally substituted hydrocarbon group. Therapeutic composition comprising the Complementary peptide according to the invention and use thereof for manufacturing a vaccine to be used in a therapeutic or prophylactic treatment of myasthenia gravis in mammals.

5 Claims, 4 Drawing Sheets

SEQUENCE LISTING

```
<160> NUMBER OF SEQ ID NOS: 4

<210> SEQ ID NO 1
<211> LENGTH: 16
<212> TYPE: PRT
<213> ORGANISM: artificial sequence
<220> FEATURE:
<223> OTHER INFORMATION: complementary peptide to the residues 61-76 of
      the major immunogenic region of the acetyl choline receptor
      involved in Myasthenia gravis
<220> FEATURE:
<221> NAME/KEY: PEPTIDE
<222> LOCATION: (8)..(8)
<223> OTHER INFORMATION: tryptophan, or tryptophan modified by
      attachment, e.g. to indole-CH2 side chain, of optionally
      substituted hydrocarbon group, preferably aryl group, such as
```

2,4,6-trimethoxybenzyl group

<400> SEQUENCE: 1

Phe Asn Ser Thr Ile Ile Gly Xaa Ile Pro Ala Lys Pro His Ile Asn
1               5                   10                  15

<210> SEQ ID NO 2
<211> LENGTH: 17
<212> TYPE: PRT
<213> ORGANISM: artificial sequence
<220> FEATURE:
<223> OTHER INFORMATION: synthetic peptide complementary to the residues
      100-116 of the alpha chain of the acetyl choline receptor involved
      in Myasthenia gravis

<400> SEQUENCE: 2

Tyr Phe Ser Arg Ile Ile Gln Lys Gln Phe Gly His Val Asn Asn Gly
1               5                   10                  15

Lys

<210> SEQ ID NO 3
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: Residue 1 is modified by a NH2 group.

<400> SEQUENCE: 3

Ile Asp Val Arg Leu Arg Trp Asn Pro Ala Asp Tyr Gly Gly Ile Lys
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (16)..(16)
<223> OTHER INFORMATION: Residue 16 is modified by a NH2 group.

<400> SEQUENCE: 4

Asn Ile His Pro Lys Ala Pro Ile Trp Gly Ile Ile Thr Ser Asn Phe
1               5                   10                  15

VACCINE FOR A THERAPEUTIC OR A PROPHYLACTIC TREATMENT OF MYASTHENIA GRAVIS

The present invention relates to a complementary peptide having at least a sequence complementary to a major immunogenic region of an acetylcholine receptor of myasthenia gravis and more particularly for a vaccine composition thereof for a therapeutic or a prophylactic treatment of myasthenia gravis, particularly in pets or humans.

Myasthenia gravis (MG) is a neuromuscular disorder characterized by weakness and fatigability of skeletal muscles. The underlying defect is a decrease in the number of available acetylcholine receptors (AChRs) at neuromuscular junctions due to an antibody-mediated autoimmune attack.

In the neuromuscular junction, acetylcholine (ACh) is synthesized in the motor nerve terminal and stored in vesicles (quanta). When an action potential travels down a motor nerve and reaches the nerve terminal, ACh from 150 to 200 vesicles is released and combines with AChRs that are densely packed at the peaks of postsynaptic folds.

When ACh combines with the binding sites on the AChR, the channels in the AChRs open, permitting the rapid entry of cations, chiefly sodium, which produces depolarization at the end-plate region of the muscle fiber. If the depolarization is sufficiently large, it initiates an action potential that is propagated along the muscle fiber, triggering muscle contraction. This process is rapidly terminated by hydrolysis of ACh by acetylcholinesterase (AChE) and by diffusion of ACh away from the receptor.

In MG, the fundamental defect is a decrease in the number of available AChRs at the postsynaptic muscle membrane. In addition, the postsynaptic folds are flattened, or "simplified." These changes result in decreased efficiency of neuromuscular transmission. Therefore, although ACh is released normally, it produces small end-plate potentials that may fail to trigger muscle action potentials. Failure of transmission at many neuromuscular junctions results in weakness of muscle contraction.

The neuromuscular abnormalities in MG are brought about by an autoimmune response mediated by specific anti-AChR antibodies. The anti-AChR antibodies are called pathogenic antibodies and reduce the number of available AChRs at neuromuscular junctions by three distinct mechanisms: (1) accelerated turnover of AChRs by a mechanism involving cross-linking and rapid endocytosis of the receptors; (2) blockade of the active site of the AChR, i.e., the site that normally binds ACh; and (3) damage to the postsynaptic muscle membrane by the antibody in collaboration with complement. The pathogenic antibodies are IgG and are T-cell dependent.

The clinical manifestations of the autoimmune disease MG are correlated with the presence of these pathogenic antibodies located at the neuromuscular junction.

Up to date, there exists only a few therapies which are either symptomatic treatment or immunotherapy.

These therapies deliver clinical benefit to patients which can be long lasting but requires a fairly involved clinical procedure. Moreover, these current treatment regimens remain only partially effective in many affected patients and lifestyle changes are necessary for large percentages of those with these diseases.

The ideal treatment of autoimmune diseases would be the selective suppression of the pathogenic components of the immune response (i.e. the pathogenic antibodies) through the directed anergy or ablation of autoreactive cell clones.

Vaccination with a peptide designed as an antigen receptor mimetic (ARM) for the major antigens of autoimmunity has shown remarkable clinical efficacy against animal autoimmune disease models, see U.S. Pat. No. 5,212,072.

Such treatment induces the anergy of autoreactive clones specific to these immunodominant proteins, despite their heterologous origin, as well as a blunting of the responses against other nearby antigens. It seems that the use of peptide vaccines whose contours closely complement those of the major antigens in autoimmunity may lead to antigen-specific, antigen receptor class-indifferent anti-idiotype (Id) responses.

These peptides, termed complementary peptides, can bind the target determinant and in a sense behave as antigen (Ag) receptor mimetics (ARM). Consequently, when used as vaccines they elicit anti-idiotypic (Id) and anti-clonotypic antibody (antibody) responses against the combining sites of antigen on certain autoreactive lymphocytes Therefore, myasthenia gravis was studied on rats, in which the myasthenia gravis can be induced in an artificial manner. It is the Experimental Autoimmune Myasthenia Gravis (EAMG).

In the EAMG, rats immunized with purified AChR develop a similar disease. Based on the idea that antigen and antibody interact in terms of hydropathic complementarity, it has been sought to induce anti-id immunity towards the pathogenic antibodies by vaccinating with a peptide complementary to the major immunogen region (MIR) of the AChR. The major immunogen region of the receptor AChR has been found to be the residues 61 to 76 of the α-chain of the receptor AChR. The complementary peptide was called RhCA 67-16. The rats were vaccinated with the complementary peptide RhCA 67-16 which was conjugated to keyhole limpet hemocyanin (KLH). Both serum and monoclonal antibodies preparations from animals vaccinated with the complementary peptide were shown to bind the pathogenic antibodies, and the incidence of the disease in those rats was greatly diminished in vaccinated animals (25%) compared to KLH immunized as well as untreated controls (90%), while the clinical severity scoring in animals with disease averaged 1.0 in vaccinated animals compared to 3.5 in positive controls. Moreover, passive administration of monoclonal anti-id antibody to rats during the course of disease induction similarly reduced EAMG incidence and severity [Araga A et al., Prevention of Experimental Autoimmune Myasthenia Gravis by a Monoclonal Antibody to a Complementary Peptide for the Main Immunogenic Region of the Acetylcholine Receptor. J Immunol. 157, 386-392 (1996)].

In view of the foregoing results of vaccination with the complementary peptide RhCA 67-16, it has been concluded that the immunogen was structurally similar to the paratope of the pathogenic antibodies, and therefore this vaccine can be considered a B-cell Ag receptor mimetic (ARM).

In order to confirm the results obtained with the complementary peptide RhCA 67-16, a second batch of RhCA 67-16 peptide was produced. The peptide of the second batch showed the expected theoretical molecular weight (MW).

The peptide of the second batch RhCA 67-16 was again tested in rats but unfortunately, the previous obtained good results on the incidence of the disease were not observed.

It is an object of the invention to provide a peptide having an antigenic behavior which may be useful in the treatment of myasthenia gravis in mammals, in particular in pet dogs and humans (MG being anecdotal in cats).

To this end, the invention provides a complementary peptide characterized in that the complementary peptide has at least a sequence SEQ. ID. NO:1 with a tryptophan in position 8 carrying at least one optionally substituted hydrocarbon group.

Advantageously, the sequence of the peptide is complementary to the residues 61-76 of the α-chain of the AChR. The peptide having at least a sequence complementary to the major immunogenic region (MIR) of receptor AChR is the peptide RhCA 67-16. This complementary peptide comprises a tryptophan in position 8. It was, to date, not well understood why, but it has been surprisingly found that the hydrocarbon group has a crucial importance for the binding of the peptide to anti-id antibody to the pathogenic antibodies targeted towards the residues 61-76 of the α-chain of the receptor AChR of dogs.

The optionally substituted hydrocarbon group is preferably an optionally substituted aryl group or an optionally substituted alkyl group, particularly an optionally substituted benzyl group, more preferably a benzyl group substituted with at least one alkoxy group, most preferably a 2,4,6-trimethoxybenzyl group.

Since canine and human MG are characterized as having an AChR antibodies (pathogenic antibodies) response that is predominantly (68%) against the MIR (residues 61-76 of the α-chain of the AChR), it was sought that it can be advantageous to provide a complementary peptide directed towards the MIR, in order to obtain a therapeutic composition which can be useful for the treatment of MG in mammals in order to develop a further human vaccine. The canine MG is very similar to the human MG.

The similarities include natural occurrence of the disorder, shared environments between humans and dogs, similar clinical presentations, diagnostic AChR autoantibody of related epitope specificity and co-morbidity of MG with other autoimmune diseases.

It is therefore another object of the invention to provide a therapeutic composition comprising the complementary peptide, having at least the sequence SEQ ID NO:1 and at least one carrier.

As mentioned here before, in canine and human MG, the pathogenic antibodies are targeted towards the MIR of the AChR. By providing a peptide complementary to this MIR, it should be possible to induce antibodies (anti-idiotypic antibodies) directed towards the complementary peptide. The anti-idiotypic antibodies will have an antigenic binding site which would be similar to the MIR of the AChR as the peptide is complementary to this binding site. Therefore, the anti-idiotypic antibodies shall be able to neutralize the pathogenic antibodies and a B-cell mediated immune response should be induced.

To obtain a composition which would give good results in mammals, it has been required to optimize the composition. Therefore, it has been found that the peptide having at least the sequence SEQ ID NO:1 should be present in an amount ranging from 750 to 25 micrograms, preferably from 500 to 50 micrograms, advantageously from 100 to 50 micrograms in 0.5 ml of phosphate buffer saline.

Advantageously, the therapeutic composition is intended to be used as a vaccine composition for the therapeutic or prophylactic treatment of MG. The vaccine composition preferably comprises an adjuvant and a peptide carrier in order to boost the immune response. As this composition is intended to increase the B-cell mediated response, it should be useful to use such adjuvant known in this purpose. Such adjuvants and carriers are well known for the person skilled in the art.

Exemplary adjuvants can be water-in-oil adjuvant, in particular TiterMax® adjuvant, alum adjuvant, Freund adjuvant and the like.

Exemplary carriers can be diphtheria toxoid, tetanus toxoid, keyhole limpet hemocyanin and the like.

These adjuvants and carriers for the therapeutic application in MG in rats are discussed in details in McAnally J L, Xu L, Villain M, Blalock JE.: The role of adjuvants in the efficacy of a peptide vaccine for myasthenia gravis. Exp Biol Med 2001; 226:307-311, which is incorporated herein in reference.

It has also been reported that the T-cell immunity response acts in myasthenia gravis. Indeed, the pathogenic antibodies are IgG-T-cell dependent. Therefore, additionally to the AChRα 61-76 region involved in the B-cell mediated immune response, it was sought that there would be another region of the receptor which is specifically recognized by the T-cell.

It has been reported in [Araga S. et al., A peptide vaccine that prevents experimental autoimmune myasthenia gravis by specifically blocking T-cell help, FASEB journal vol 14, 2000] that the production of pathogenic antibodies in the Lewis rat is helped by T-cells specific to residues 100 to 116 of the α-chain of the AChR. Araga S. et al. have thus immunized Lewis rats with a peptide complementary to the residues 100-116 of the α-chain of the receptor AChR (which was called RhCA 611-001). It was observed that the resulting anti-ARM antibody/antigen receptor interactions interfered with autoreactive T-cell help and anergized autoreactive B-cells thus reducing AChR reactive autoantibody titers which led to marked clinical improvement, lowered mortality and preservation of AChR levels on muscles in the Lewis rat.

The peptide complementary to these residues 100-116 of the α-chain of the receptor AChR is the peptide RhCA 611-001 having at least the sequence SEQ ID NO:2.

This peptide was tested in rats in order to determine the potential of a therapeutic vaccine composition comprising the peptide complementary to the T-cell recognition site of the receptor AChR.

It has been found that the complementary peptide having at least the sequence SEQ ID NO:2 can be a likely candidate in a therapeutic composition for MG.

Hence, it has been thought that a combination of the complementary B-peptide RhCA 67-16 and a peptide complementary to a T-cell recognition site can result in a reduced incidence of EAMG in rats.

Unfortunately, (see comparative example 3) the incidence and the severity of EAMG in rats were not reduced by the combination of both peptides (either sequentially or simultaneously).

When both peptides were administered together, in rats, the average severity and the % mortality were similar to the values observed with the peptide having at least the sequence SEQ ID NO:2 suggesting that there was no synergic effect of both peptides in rats.

Although the AChR is highly conserved during evolution and although the T-cell immunity is, on its turn, very species-dependent, it was surprisingly found that a composition comprising the complementary peptide having at least the sequence SED ID NO:1 and the peptide having at least the sequence SEQ ID NO:2, which sequence is complementary to a T-cell recognition site of the acetylcholine receptor, as well as at least one carrier provides an enhanced effect on MG in dogs.

Indeed, a synergic effect of B-complementary peptide and of T-complementary peptide was found in dogs.

This result is even more surprising considering the fact that the peptide having a least the sequence SEQ ID NO:2 is complementary of a T-cell recognition site of AChR in rats. The T-cell immunity, although AChR is highly conserved during evolution, ought to be different in rats and in dogs.

Advantageously, the sequence SEQ ID NO:2 is complementary to residues 100 to 116 of an α-chain of said T-cell recognition site of the acetylcholine receptor.

The production of the pathogenic antibodies is helped by T-cells, specific to residues 100-116 of the α-chain of the receptor AChR.

Advantageously, the vaccine composition comprises from 750 to 25 micrograms, preferably from 500 to 50 micrograms, advantageously from 100 to 50 micrograms of each peptide having at least the sequence SEQ ID NO:1 and/or SEQ ID NO:2, respectively, in 0.5 ml of phosphate buffer saline with at least one adjuvant.

Preferably both peptides are coupled with a peptide carrier being the same or different.

According to a variant embodiment of the invention, the composition comprising both peptides comprises a first and a second formulation.

The first formulation comprises the peptide having at least the sequence SEQ ID NO:1 according to the invention and the second formulation comprises the peptide having at least the sequence SEQ ID NO:2.

Advantageously, each first and second formulation comprises independently from 750 to 25 micrograms, preferably 500 to 50 micrograms, advantageously from 100 to 50 micrograms of complementary peptide in 0.5 ml phosphate buffer saline with at least one adjuvant.

Preferably the peptide of each formulation should be coupled with a suitable peptide carrier.

The composition comprising the first and the second formulation is provided to be used as a vaccine composition for the therapeutic or prophylactic treatment of MG in mammals, each formulation being intended to be administered simultaneously or sequentially.

In each variant embodiment, the composition is provided for the induction of an activation of cell mediated immunity depending on B and T lymphocytes.

The invention also provides a detection kit comprising the complementary peptide having at least the sequence SEQ ID NO:1 provided for detecting anti-idiotypic antibodies of the major immunogenic region of myasthenia gravis.

The peptide having at least the sequence SEQ ID NO:1 is advantageously in the state of a peptide complex for being used as coating complex in an ELISA test, for the binding of anti-idiotypic antibodies in sera of pet dogs or human, immunized with the composition according to the invention. A phosphatase alkaline labeled human or dog anti IgG should be added to the wells of an ELISA plate to reveal the binding and therefore detect antibodies anti-Id with a chromogen substrate.

Alternatively, the anti IgG can be labeled with a horseradish peroxidase.

In a variant the peptide is directly in the state of a peptidic complex comprising on one hand the peptide having at least the sequence SEQ ID NO:1 and on the other hand a label like a phosphatase alkaline label or a peroxidase label for being use in an ELISA Test or in a Western blot for the detection of anti-idiotypic antibodies.

It is also an object of the invention to provide a method for manufacturing a complementary peptide having at least the sequence SEQ ID NO:1, comprising the steps of:
  synthesizing of the complementary peptide having at least the sequence SEQ ID NO:1, and
  hydrocarboning a tryptophan residue located in position 8, in said sequence SEQ ID NO:1.

It is still an object of the invention to provide a method for manufacturing a medicament to be applied in myasthenia gravis comprising the steps of:
  synthesizing the complementary peptide having at least the sequence SEQ ID NO:1, and
  coupling of the complementary peptide having at least the sequence SEQ ID NO:1 with at least one carrier.

It is still a further object of the invention to provide a method for manufacturing a medicament to be applied in myasthenia gravis comprising the steps of:
  synthesizing the complementary peptide having at least the sequence SEQ ID NO:1,
  synthesizing the complementary peptide having at least the sequence SEQ ID NO:2, and
  coupling of both complementary peptide with at least one carrier.

In a variant embodiment, the invention provides a method for manufacturing a medicament to be applied in myasthenia gravis comprising the steps of:
  manufacturing a first formulation by synthesizing the complementary peptide having at least the sequence SEQ ID NO:1, and by coupling it with at least one carrier, and
  manufacturing a second formulation by synthesizing the complementary peptide having at least the sequence SEQ ID NO:2, and by coupling it with at least one carrier.

Advantageously, it is also an object to the invention to relate to a method for manufacturing a medicament intended for therapeutic or prophylactic application in myasthenia gravis comprising the steps of:
  synthesis of the complementary peptide of SEQ ID NO:1
  synthesis of the complementary peptide of SEQ ID NO:2
  coupling of the complementary peptides with a carrier
  mixing of both complementary peptides coupled to the carrier with a saline solution and an adjuvant.

Other embodiments according to the invention are further described in the enclosed claims.

The invention also relates to a method of treatment of myasthenia gravis in mammals comprising the administration of a therapeutic composition comprising the complementary peptide having at least the sequence SEQ ID NO:1 and optionally the complementary peptide having at least the sequence SEQ ID NO:2.

As aforementioned, the complementary peptide having at least the sequence SEQ ID NO:1 is complementary to the major immunogenic region (MIR) of the residues 61-76 of the α-chain of the acetylcholine receptor (AChR) of myasthenia gravis (MG).

The sequence of the residues 61-76 of the α-chain of the acetylcholine receptor (AChR α 61-76) is the following:

$NH_2$-Ile-Asp-Val-Arg-Leu-Arg-Trp-Asn-Pro-Ala-Asp-Tyr-Gly-Gly-Ile-Lys

The peptide complementary to the AChR α 61-76 has the following sequence and was called RhCA 67-16

Asn-Ile-His-Pro-Lys-Ala-Pro-Ile-Trp-Gly-Ile-Ile-Thr-Ser-Asn-Phe-$NH_2$

Therefore, SEQ ID NO:1 is the following:

$NH_2$-Phe-Asn-Ser-Thr-Ile-Ile-Gly-Trp-Ile-Pro-Ala-Lys-Pro-His-Ile-Asn

The peptide having at least the sequence SEQ ID NO:1 was synthesized on a Biosearch Peptide Synthesizer, Model 9500, using FMOC (fluorenyl methyloxy carbonyl chloride) chemistry and was purified by reverse-phase high performance liquid chromatography using a Dynamax C18 300 angstrom 15μ column (19×300 mm) and a gradient of 90% $H_2O$ (0.1% trifluoroacetic acid)/10% acetonitrile (0.1% trifluoroacetic acid) to 10% $H_2O$ (0.1% trifluoroacetic acid)/90% acetonitrile (0.1% trifluoroacetic acid) over 60 minutes at a flow rate=5 ml/min, the retention time being 39-42 minutes and the molecular weight of the peptide with a 2,4,6-trimethoxybenzyl was 1988.

The RhCA 67-16 which is the ARM peptide for AChR α 61-76 comprises a tryptophan in position 8 which is hydrocarbonated, preferably alkylated or arylated. The hydrocarbon group suitable for such an hydrocarbonation can be selected in the group consisting in an optionally substituted aryl group and an optionally substituted alkyl group, particularly an optionally substituted benzyl group, preferably a benzyl group substituted with at least one alkoxy group, more preferably a 2,4,6-trimethoxybenzyl group.

Preferably, the hydrocarbon group is a 2,4,6-trimethoxybenzyl group and the chemical sequence is the following 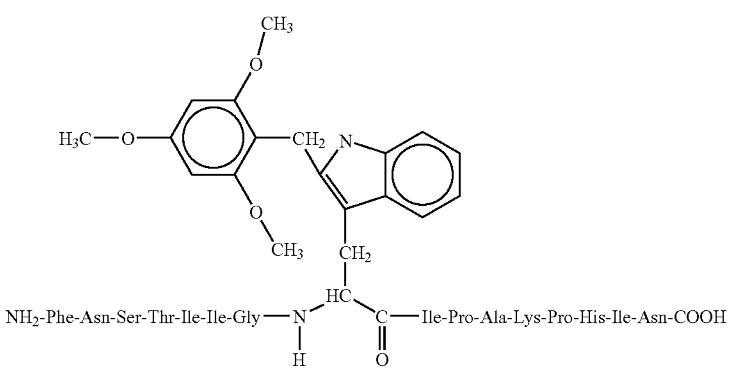 The B-cell peptide was synthesized and a 2,4,6-trimethoxybenzyl group was added to the tryptophan in position 8 by adding T mob when cleaving the peptide from the solid support under acidic condition (for example during elution with trifluoroacetic acid).

The hydrocarbonation, particularly the arylation of the peptide occurs during the cleavage of the peptide from the solid support under acidic condition in the presence of Tmob. The peptide RhCA 67-16 was coupled to keyhole limpet hemacyanin (KLH) as a carrier protein as previously described. The KLH was coupled to the B-cell peptide using a glutaraldehyde conjugation in order to preserve the chemical, physical and biological features of both KLH and peptide. The B-cell peptide and the carrier protein (KLH) are added to a glutaraldehyde solution. The reaction is shown hereunder:

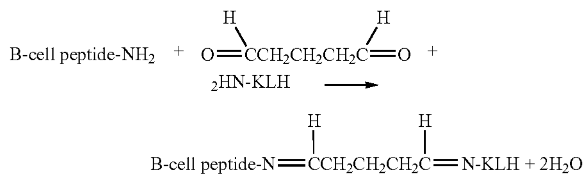

The glutaraldehyde does not react with the proteins or the peptides under its free form, but as an unsaturated polymer, which gives imino bonds stabilized by conjugation.

According to the invention, the carrier protein can be the aforementioned KLH, but it has to be understood that other carrier proteins can be used, such as, for example, diphtheria toxoid or tetanus toxoid or any big molecule of protein nature that acts as a support for the peptide so that the peptide is not alone and too small. Hence, the peptide with the carrier protein will not be immediately destroyed by the immunologic system and is more imunogenic.

One skilled in the art should also understand in view of the aforementioned that both peptides (B-cell peptide and T-cell peptide) can be coupled to the same carrier protein or to different carrier protein, being of identical or different nature.

For the present study, the clinical trials were done in dogs. A single dose of vaccine comprised 500 micrograms in 0.5 ml phosphate buffered saline of the peptide RhCA 67-16-KLH conjugate, emulsified in 0.5 ml of an water-in-oil adjuvant, preferably TiterMax™ adjuvant (TiterMax USA, Inc., Norcross, Ga.).

The peptide having the sequence SEQ ID NO:2 is complementary to the T-cell epitope (residues 100-116) of the α-chain of the AChR. The peptide was synthesized on a Biosearch Peptide Synthesizer, Model 9500, using FMOC (fluorenyl methyloxy carbonyl chloride) chemistry and was purified by reverse-phase high performance liquid chromatography using a Dynamax C18 300 angstrom 15μ column (19×300 mm) and a gradient of 90% $H_2O$ (0.1% trifluoroacetic acid)/10% acetonitrile (0.1% trifluoroacetic acid) to 10% H$_2$O (0.1% trifluoroacetic acid)/90% acetonitrile (0.1% trifluoroacetic acid) over 60 minutes at a flow rate=5 ml/min, the retention time is 18-20 minutes and the MW is 2036.

The complementary peptide having SEQ ID NO:2 has the following sequence:

NH$_2$-Tyr-Phe-Ser-Arg-Ile-Ile-Gln-Lys-Gln-Phe-Gly-His-Val-Asn-Asn-Gly-Lys

As previously described, the peptide RhCA 67-16 also called herein B-peptide and the peptide RhCA 611-001 also referred herein T-peptide were tested alone on rats. The results indicated that either B-peptide alone or T-peptide alone give a significant decrease in the pathogenic antibodies level. When tested in unpublished trials on rats, B and T-peptides together did not give better results in the pathogenic antibodies levels than when T-peptide alone was administrated. These results indicated that there was no synergic effect in rats when using both peptides.

The present invention provides results in dogs which indicates that there is an unexpected synergic effect when both peptides were used in dogs either in a simultaneous or in a sequentially administration.

The invention will be further detailed in the following non limiting examples.

EXAMPLE 1

Figure 1A:
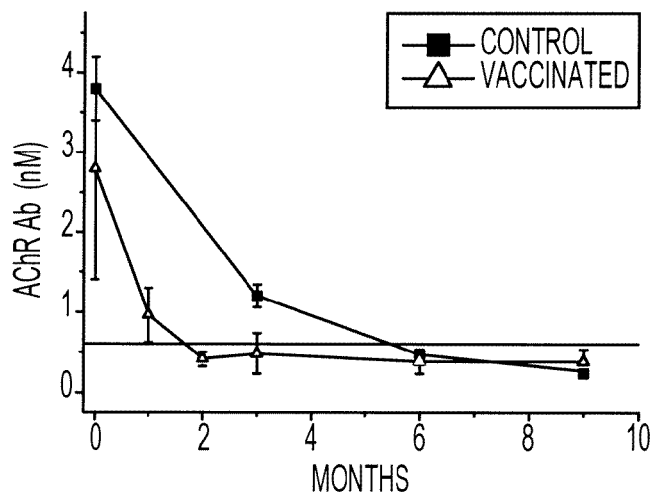
FIG. 1A compares the trend in AChR antibody levels in vaccinated and control animals.

Materials and Methods. Twenty nine dogs diagnosed with autoimmune MG with positive AChR antibody titers (>0.6 nM) by an established clinical radioimmunoassay were initially enrolled in the study. Five animals (17%) died of aspiration pneumonia and one died acutely following surgery for a thymoma prior to complete vaccination. The death rate in the present study is comparable to the 6/35 (17%) and 2/12 (17%) reported previously in the historical controls. Three dogs were lost to follow-up and four were dropped from the study for noncompliance; one was withdrawn from the study by the owner before complete vaccination because of a skin reaction at the site of immunization. Five animals spontaneously remitted after diagnosis but before the initiation of vaccination. Thus, 10 dogs (5 males and 5 females, 1 to 10 years old) completed the study and none of these animals had thymoma or were on corticosteroids or other immunosuppressants. The time from onset of clinical symptoms to confirmed diagnosis with AChR antibody assay for these animals was 2 to 4 weeks. Remission is defined as long term return of the AChR antibodies titer to the normal range (<0.6 nM) with clinical normality in the absence of acetylcholinesterase inhibitors. Transient remission refers to one or more measurements of AChR antibody titers below 0.6 nM prior to complete resolution of MG and long term return of AChR antibody to normal values. Pet owners gave informed consent and the study was approved by the Institutional Animal Care and Use Committee of the University of Florida.

The various vaccine compositions listed in table 1 were used in the trials.

TABLE 1

Dog trial compositions

| No. Composition | peptide of SEQ ID NO: 1 (micrograms) | peptide of SEQ ID NO: 2 (micrograms) | carrier | phosphate saline buffer | adjuvant |
| --- | --- | --- | --- | --- | --- |
| 1 | 500 | 0 | KLH | 0.5 ml | Titer Max ® |
| 2 | 0 | 500 | KLH | 0.5 ml | Titer Max ® |
| 3 | 500 | 500 | KLH | 0.5 ml | Titer Max ® |

In the clinical trials on dogs, the compositions were administered subcutaneously at a minimum of four sites. Vaccinations were initiated at the time of confirmed diagnosis up to four months post diagnosis for certain animals. Animals were immunized and boosted at 2 week intervals.

The purpose of the present invention was to evaluate the aforementioned T and B-cell vaccines for the ability to diminish AChR antibody levels as compared to historical controls in a clinical trial in spontaneously acquired autoimmune MG in pet dogs (Shelton G D et al., Neurology 2001; (57): 2139-2141). A control group of myasthenic pet dogs immunized with carrier protein (without ARM peptides) in adjuvant was not included at this time because of the probable lack of benefit based on rat EAMG studies (Araga S, et al.) of carrier protein without coupled complementary peptide in 0.5 ml of phosphate buffer saline with adjuvant.

All statistical analyses were performed using Instat biostatistics software (GraphPad software, San Diego, Calif.). For comparison of serum antibody values and times to remission between groups, unpaired t-tests were used except when the limitations of the dataset indicated the use of the unpaired t-test with Welch correction or the Mann-Whitney test; the null hypothesis was that vaccination did not decrease AChR antibody titers or time to remission. Paired t-tests were used for the analysis of serum antibody titers before and after vaccination. For endpoint evaluations such as remission statistics, contingency table analysis was performed with Fisher's exact test.

Results
Prospective Outcomes

The prospectively studied historical control group consisted of 40 myasthenic dogs of both sexes of whom 35 were followed long-term and outcomes were known. These animals were identified as AChR antibody positive in a cohort of 152 dogs with idiopathic megaesophagus. These animals were compared to the 20 dogs (excluding the animal that died following surgery for thymoma) from our study for whom the outcome was known. The AChR antibody assays were performed by the same veterinary service (UC San Diego, Comparative Neuromuscular Laboratory) for all dogs (historical controls and the present study).

TABLE 2

Prospective outcomes for vaccinated myasthenic dogs and historical controls

| Group | Total Dogs | Remitted (%) | Not Remitted (%) | Euthanasia (%) | Aspiration Pneumonia Death (%) |
|---|---|---|---|---|---|
| Historical Controls | 35 | 6 (17%) | 11 (31%) | 12 (34%) | 6 (17%) |
| Vaccinated | 20 | 15 (75%)$^A$ | 0$^B$ | 0$^C$ | 5 (25%)$^D$ |

$^A$p < 0.0001,
$^B$p = 0.0044,
$^C$p = 0.0022, and
$^D$p = 0.504, all by Fisher's exact test. Each comparison considers dogs with indicated outcomes against all other dogs in the group.

Table 2 shows that there was no significant difference between the number of animals that died of aspiration pneumonia or choking in our population as compared to the historical controls (25% vs. 17%, respectively). Five of 20 dogs in our study spontaneously remitted to long-term AChR antibody levels in the normal range (<0.6 nM) after diagnosis but before vaccination. Thus, there was also no difference in the spontaneous remission rate between the two groups (25% vs. 17%). These results suggest that the two cohorts are well matched. A significant difference was in the number of euthanized animals. Twelve dogs (34%) in the historical control group were euthanized due to the poor prognosis that was given. No animals in the clinical trials according to the invention were euthanized. There was a highly significant difference in overall long-term remission rates between the two groups. While the historical controls had only 6 of 35 dogs (17%) remit with AChR antibody levels returning to the normal range 75% of the 20 vaccinated dogs remitted. Considering only animals that survived aspiration pneumonia or euthanasia, the historical control had a remission rate of 35% (6/17) versus the 100% remission rate (15/15) (p<0.0001) in the present study. This increased remission rate was entirely accounted for by the 10 out of 10 dogs that remitted in association with vaccination. If we consider the best possible scenario for the historical controls and the worst possible scenario for vaccinated animals, there is still significantly increased remission. Specifically, if the 5 dogs lost to follow-up in the control group were assumed to have remitted (11 of 40 remitted, 27.5%) while the 9 dogs in our group either lost to follow-up or dropped from the study were assumed to have not remitted (15 of 29 remitted, 51.7%), vaccination still caused a statistically significant increase in the remission rate (p=0.0482, Fisher's Exact Test).

Vaccination leads to an accelerated time to remission when compared to spontaneous recovery from canine MG.

The historical control group consisted of 47 myasthenic dogs that spontaneously remitted, were analyzed retrospectively, and were comparable to the 10 vaccinated animals in several important respects. The dogs in both groups were not treated with corticosteroids or other immunosuppressants; the AChR antibody assays were performed by the same veterinary service; the time elapsed from clinical signs to confirmed diagnosis for vaccinated dogs (2 to 4 weeks) fell within the period for historical controls (1 week to 5 months); and the two groups consisted of roughly comparable ratios of males and females with similar age ranges and were studied during an overlapping period of time (historical control, 1990-2000 and vaccinated animals, 1997-2003).

Interestingly, in evaluating the data set for the historical controls, the AChR antibody levels were observed to follow one of two courses. Some cases had a monophasic decline in AChR antibody levels that led to remission, while others showed a fluctuating pattern of increasing and decreasing AChR antibody levels prior to long term remission. AChR antibody levels with time in vaccinated dogs also segregated into one or the other of these same two groups (see below). Thus appropriate analysis dictated that comparisons should be made within groups.

Figure 1B:
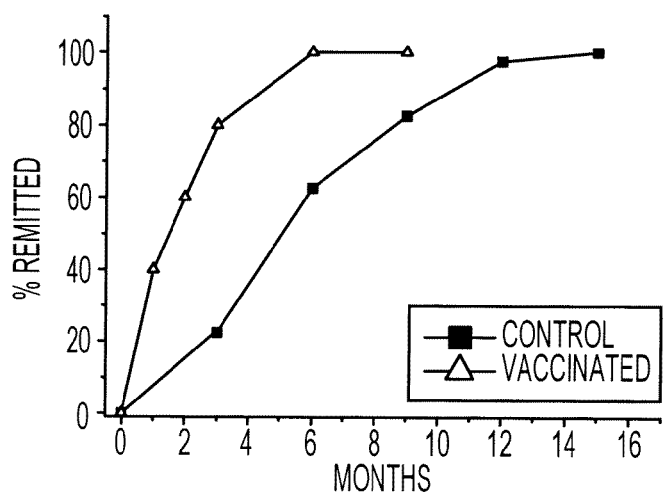
FIG. 1B compares the trend in % remitted in vaccinated and control animals.
Figure 1C:
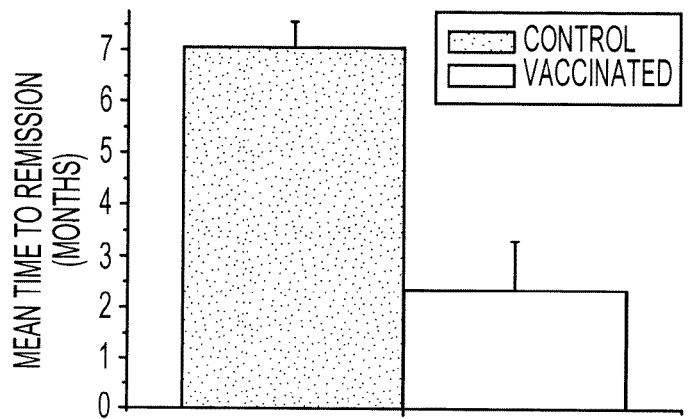
FIG. 1C compares the mean time to remission in vaccinated and control animals.
Figure 2A:
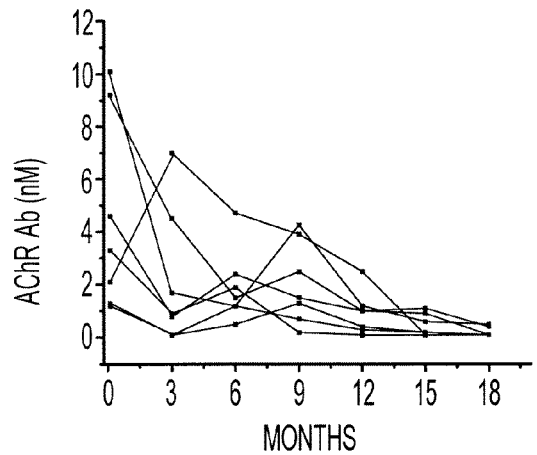
FIG. 2A shows the trend in AChR antibody levels in six control animals, and FIG. 2B that in five vaccinated animals FIG. 2C compares the mean time to first remission and to long term remission for control and vaccinated animals.
Figure 2B:
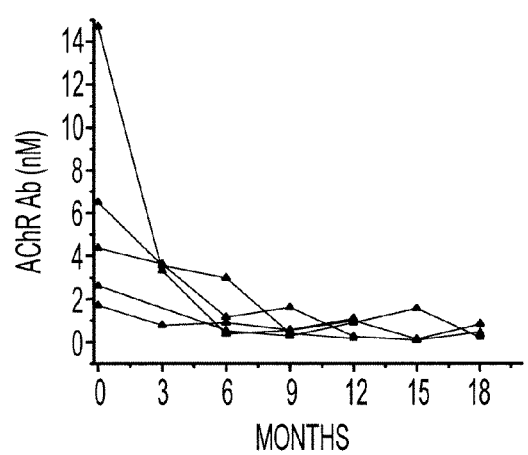
FIG. 2D shows the mean number of transient remission over a 3 month period for control and vaccinated animals.
Figure 2C:
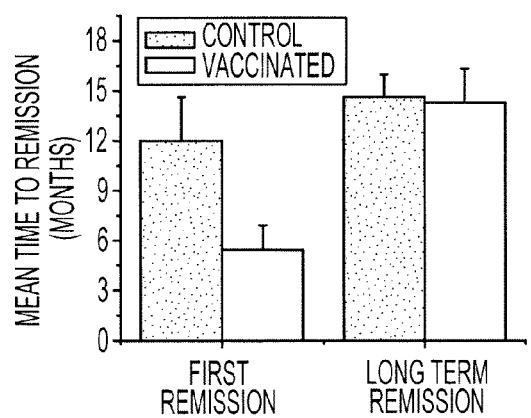
Figure 2D:
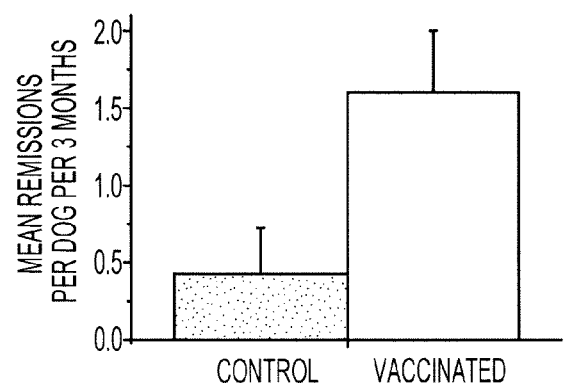

FIG. 1 (upper panel) shows that at the time of confirmed diagnosis of dogs showing a monophasic decline, there was not a statistical difference in AChR antibody levels between the vaccinated group (n=5) and historical controls (n=40). However, the vaccinated group showed an accelerated rate of decline in AChR antibody titers. This was mirrored by a faster rate of remission in the vaccinated group (FIG. 1, middle panel). This accelerated remission among vaccinated dogs is most evident at the 3 month time point, where the relative likelihood of remission was 3.56 for vaccinated dogs vs. controls by Fisher's exact test (p=0.019).

FIG. 2 shows the AChR antibody levels with time after confirmed diagnosis for historical controls (2a) and vaccinated animals (2b) showing a fluctuating pattern of autoantibody concentrations. While the initial AChR antibody titers (nM±SEM) were not significantly different between the vaccinated dogs (5.98±2.33) and historical controls (4.54±1.4), there appeared to be a marked diminution in the overall amplitude of the fluctuations for the vaccinated dogs at times post diagnosis. In contrast, the mean time to long term remission was the same for the two groups. Thus it seems that while the duration of the disease is the same in the two groups, vaccinated dogs may spend more time in remission during the course of the disease. This was borne out by the observation that 100% (5/5) of vaccinated dogs as compared with 29% (2/7) of historical controls had at least one period of remission before complete resolution of disease. To assure that the increase in animals showing a transient return to normal AChR antibody levels was not due to more frequent sampling of the vaccinated group relative to the historical controls (sampling at 3 month intervals), the AChR antibody levels were considered only at 3 month intervals post diagnosis. The results showed that 5/5 vaccinated dogs versus 2/7 historical controls had at least one blood sample within the normal range (<0.6 nM) for AChR antibodies after vaccination and before complete resolution of disease. In total, there were 8 episodes of normal AChR antibody titers in the 5 vaccinated animals [1 dog with 3, 1 dog with 2 and 3 dogs with 1 episode(s)] compared to 3 episodes in the 7 historical controls [1 dog with 2, 1 dog with 1 and 5 dogs with 0 episode(s)]. Thus the mean number of episodes of transient remissions per dog per 3 month interval was significantly higher (p<0.0251, Mann-Whitney Test) in the vaccinated animals than the historical controls (FIG. 2d).

Prior to long term resolution of MG and considering all available blood samples (not simply the 3 month intervals), four of five vaccinated dogs with oscillating levels of AChR antibodies showed more than one episode of transient remission (2 animals with 3 episodes and 2 animals with 2 episodes, total of 10) which corresponded to the initiation of a course of vaccination.

Figure 3A:
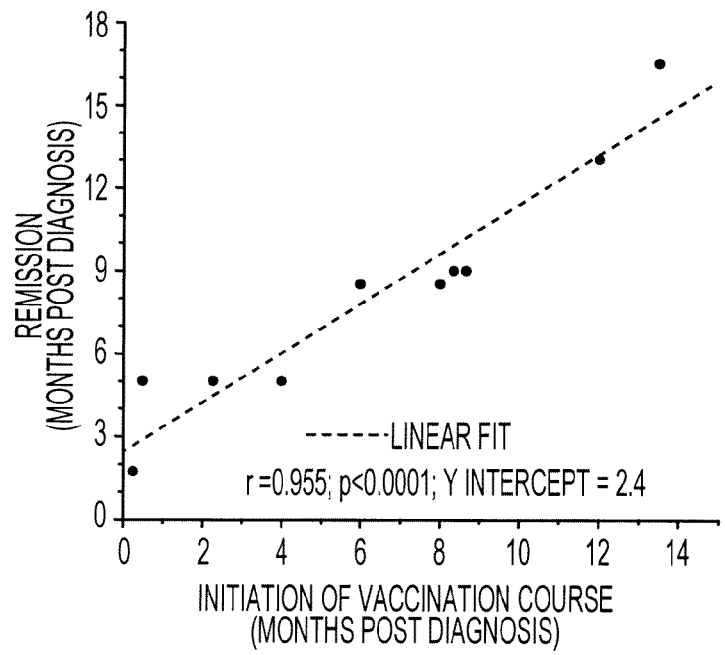
FIG. 3A shows the regression of the months post-diagnosis to remission against the months post-diagnosis of initiation of the vaccination course.
Figure 3B:
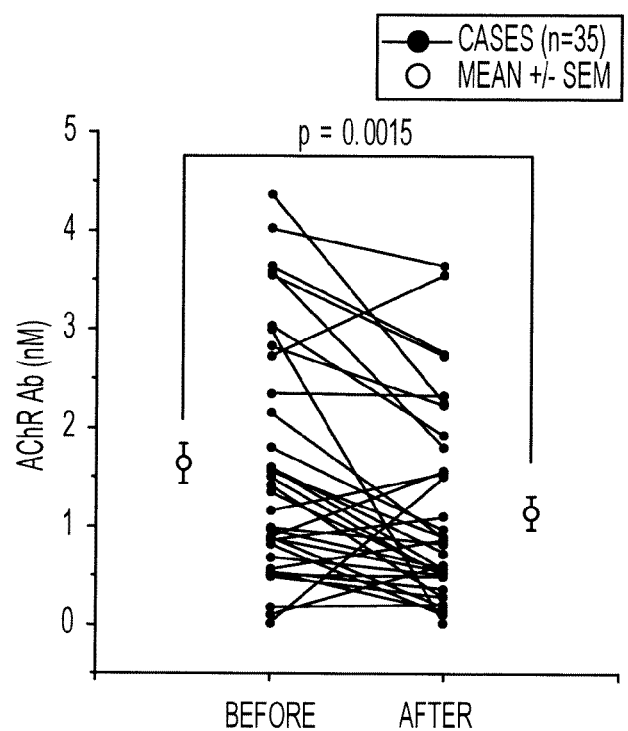
FIG. 3B shows the change in AChR antibody levels from before to after, vaccination for 35 vaccination cases.

FIG. 3 (upper panel) shows a highly significant correlation (r=0.955, p<0.0001) between the time of initiation of a vaccine course and the time of the beginning of the subsequent period of remission. Thus temporally, vaccination is very strongly associated with transient remission and is independent of when the vaccination is initiated relative to diagnosis. Importantly, the Y intercept for this relationship is 2.4 months which corresponds very closely to the mean time to remission (2.35±0.96 months) of vaccinated dogs showing a monophasic decline in AChR antibody titers (FIG. 1, lower panel). When this data is analyzed as the time elapsed between vaccination and remission, the mean time to remission was 1.775±0.43 months (lower and upper 95% CI's=0.805 and 2.745, respectively). This is not statistically different than the mean time to remission for dogs that were vaccinated and showed a monophasic decline (FIG. 1, lower panel). Thus regardless of the pattern of AChR antibody levels, vaccination leads to a very similar time to remission suggesting a similar mechanism may be involved in both courses.

There was also a quantitative relationship between single vaccination events and a reduction of AChR antibody levels at the next sampling time (2 to 4 weeks) that was observed in all 5 dogs with fluctuating AChR antibody titers. Of 35 vaccination events, 28 (80%) resulted in a diminution in AChR antibody titer (FIG. 3, lower panel). The 7 vaccination events that did not lower AChR antibody levels were distributed among the 5 animals with one being observed for each of 3 dogs and 2 for each of 2. Overall, the mean AChR antibody levels declined from 1.63±0.21 before to 1.14±0.17 nM after vaccination (P=0.0015, two-tailed Paired t Test).

Combined administration of T and B-cell vaccines is superior to their sequential administration.

Figure 4A:
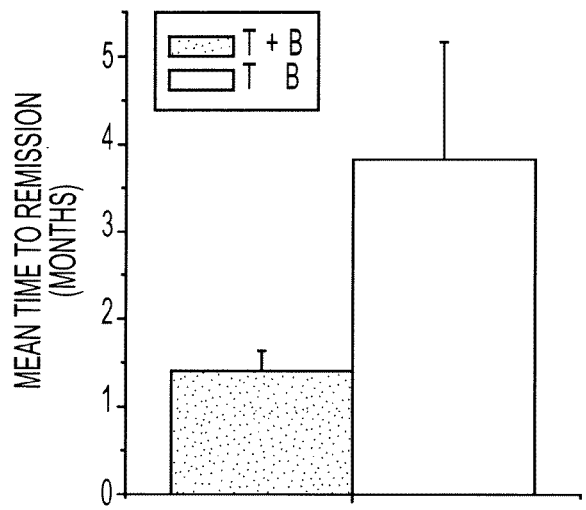
FIG. 4A compares the mean time to first remission when the T and B cell vaccines are given simultaneously (T+B) with when they are given sequentially (T B). Likewise, FIG. 4B compares the mean time to first remission per vaccine dose.
Figure 4B:
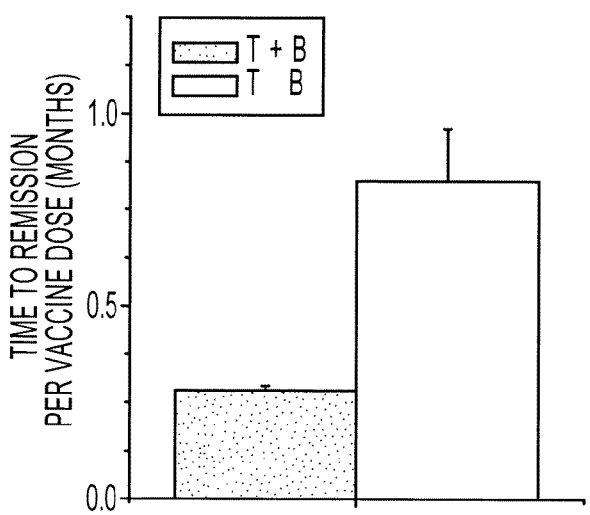

The vaccination protocol was performed in one of two ways. The T and B-cell vaccines were given at the same time or a course of 3 T-cell vaccine doses at 2 week intervals was followed by 3 B-cell vaccine doses at 2 week intervals. Since the mean time between vaccination and long-term remission for dogs showing a monophasic decline (2.35 months, FIG. 1) was not different than the mean time between initiation of a vaccination course and subsequent transient remission for dogs with fluctuating AChR antibody levels (2.4 months, FIG. 3) and in this later group was independent of the time of vaccination post diagnosis, comparisons were possible for the efficacy of the two vaccination protocols regardless of the pattern of AChR antibody levels. FIG. 4's upper panel shows that the mean time to the first remission (either long term or transient) following the initiation of vaccination approached significance (p=0.0639, unpaired t-test with Welch correction) and was 2.7 times faster when the T and B-cell vaccines were administered simultaneously rather than sequentially. Furthermore, when vaccines were administered sequentially only 4 of 7 animals showed a remission following T-cell vaccination alone. Also, on average, more vaccinations per animal were required when the T and B-cell vaccines were given sequentially (3.86±1.06) as opposed to simultaneously (2.67±0.333) to achieve a remission. When we factor in the number of T and/or B ARM vaccine doses to achieve a remission, together with the time to remission, there is a significant decrease (p=0.0167, two-tailed Mann-Whitney test) in the time to remission per dose when the vaccines are administered simultaneously rather than sequentially (FIG. 4, lower panel). Thus, optimal efficacy appears to require that both vaccines be administered together. Since the same adjuvant (TiterMax®) and carrier protein (KLH) were used in both vaccination protocols, it is unlikely that they were responsible for the effect. If so, one would have expected to observe similar mean times to first remission following the same amount of vaccines for the two protocols. Consequently, the vaccine effect is dependent on the T and B ARM peptides and independent of the adjuvant and carrier and in spontaneous MG in dogs it effectively takes a combination of B and T-cell vaccine to bring the fast remission we observe.

The average time at which 50% of the animals remitted was 2 months. This average remission time is 3.2 times faster than the historical controls (6.4 months).

EXAMPLE 2

Comparative Example in Lewis Rats

Lewis rats were immunized with purified AChR in order to develop an experimental autoimmune M.G. Then Lewis rats were treated with B and T-peptides conjugated to keyhole limpet hemocyanin (KLH). Both serum and preparations from animals vaccinated with the complementary peptide were shown to bind the pathogenic antibodies. With B-peptide composition, the incidence of the disease was greatly reduced in vaccinated animals (25%) compared to KLH immunized as well as untreated controls (90%), while the clinical severity scoring in animals with disease averaged 0.25 in vaccinated animals compared to 1.3 in positive controls. With T-peptide composition, the incidence of the disease was also reduced in vaccinated animals (55%) compared to KLH immunized as well as untreated controls (89%), while the clinical severity scoring in animals with disease averaged 1.2 in vaccinated animals compared to 2.5 in positive controls.

Moreover, passive administration of monoclonal anti-id antibody to rats during the course of disease induction similarly reduced EAMG incidence and severity (Araga et al, 1996). The results are shown in Table 3.

TABLE 3

Collected results from the animal model trials for ARM vaccine for EAMG EAMG

|  | Disease incidence | | Disease severity | |
| --- | --- | --- | --- | --- |
|  | controls (n) | treated (n) | controls (n) | treated (n) |
| B-peptide composition | 90% (39) | 25% (16) | 1.3 (39) | 0.25 (39) |
| T-peptide composition | 89% (18) | 55% (18) | 2.5 (18) | 1.2 (18) |

EXAMPLE 3

Comparative Example on Lewis Rats

To evaluate whether vaccination with T-peptide together with B-peptide with an hydrocarbon group causes a different effect on experimental autoimmune myasthenia gravis (EAMG) than either B with an hydrocarbon group and T-peptide alone and separately, Lewis rats were immunized three times with keyhole limpet hemacyanin (KLH) or T-peptide or B-peptide with an hydrocarbon group coupled to KLH either alone or in combination. EAMG was then induced with purified Torpedo AChR and disease was monitored.

The results are presented in Table 4 wherein it can be seen that either T-peptide or B-peptide alone reduced the EAMG incidence, severity and mortality as compared to control rats immunized with KLH. Simultaneous vaccination with T-peptide together with B-peptide caused a minor and statistically insignificant benefit relative to either peptide vaccine alone. Therefore, in the Lewis rat, the simultaneous vaccination with both T and B-peptides neither increased nor diminished the efficacy of either peptide vaccine alone suggesting that there is no synergic effect in rats of these both peptides.

TABLE 4

| Vaccine | Severity | | | | | Average | Mortality (%) | EAMG Incidence (%) |
|---|---|---|---|---|---|---|---|---|
| | 0 | 1 | 2 | 3 | 4 | Severity | | |
| KLH | 3 | 2 | 1 | | 4 | 2.00 ± 0.58 | 40.00 | 70.00 |
| T-peptide | 4 | 3 | | | 2 | 1.22 ± 0.55 | 22.22 | 55.56 |
| B-peptide | 4 | 2 | 1 | | 2 | 1.33 ± 0.55 | 22.22 | 55.56 |
| T and B-peptide | 5 | 2 | 1 | | 2 | 1.20 ± 0.51 | 20.00 | 50.00 |

Consequently, canine and human MG, as well as EAMG in rats, are characterized as having an AChR antibody response that is predominantly (68%) against the MIR. Furthermore, MIR-specific-antibodies can passively transfer a myasthenic phenotype. Considering this together with the ability of the B-cell vaccine to induce an anti-idiotypic antibody response to MIR-specific-antibodies and B-cells in rat EAMG, lowering AChR antibody levels and ameliorating disease, it does not seem particularly surprising that this vaccine diminished AChR antibody levels in dogs. Such efficacy in rat EAMG, as well as spontaneously acquired canine MG coupled with a predominant anti-MIR antibody response in human MG, suggests a potential utility of the B-peptide vaccine in the human disease. Indeed, naturally occurring anti-idiotypic antibodies against AChR antibodies has been reported in 40% of human MG patients, and its presence is associated with lower anti-AChR antibody titers and clinical improvement.

Moreover, the vaccine designed against the dominant T-cell epitope of the AChR for the Lewis rat is apparently effective in dogs. One possible scenario is that anti-clonotypic antibodies against the T-cell vaccine may induce or expand the newly described and naturally occurring CD25+ CD4+regulatory T-cells via an interaction with their T-cell receptor. If this were the case, these cells would specifically react with AChR α100-116 but would nonspecifically suppress other autoreactive T-cells for more dominant epitopes of the AChR at the neuromuscular junction. Such a mechanism, if operational, would suggest that the vaccines may be effective against human as well as canine MG.

These positive results in a second species raise hope for the eventual application of these vaccines in humans with ad hoc carrier/adjuvant. Should these yield the same results as the present study, ARM vaccines may represent a new class of targeted therapies that can drive autoimmune diseases into long-term remission.

For a prophylactic or a therapeutic treatment in humans, the best carrier and adjuvant suitable for human use were determined.

All the animal experiments were carried out with the same peptides that will be used in human and that are the subject of this application.

During the experiments they were coupled to different carriers and combined with different adjuvants. It is proven that the carriers and adjuvant are necessary but that their real nature is not of primary importance. Experiments were carried out to prove that a combination to a carrier and an adjuvant suitable for human use was working as well as or even better than carrier and adjuvant easy to manage and use in labs with animal experiments (McAnally J. L. et al, 2000). Table 5: Prevention of EAMG with B-cell Arm vaccine with different combination of carrier protein and adjuvant

| | EAMG | | | |
|---|---|---|---|---|
| | Disease incidence | | Disease severity | |
| | controls (n) | treated (n) | controls (n) | treated (n) |
| KLH in CFA | | 40% (10) | | 0.50 (10) |
| KLH in IFA | | 86% (7) | | 1.57 (7) |
| KLH in Alum | | 60% (10) | | 0.90 (10) |
| DT in CFA | | 40% (10) | | 0.60 (10) |
| DT in IFA | | 89% (9) | | 1.33. (9) |
| DT in Alum | | 50% (10) | | 0.50 (10) |
| PBS | 100% (10) | | 2.10 (10) | |

The combination DT/alum gave the peak response faster than KLH/alum and it was also slightly more effective against EAMG (McAnally et al, 2000). Although the preferred embodiments of the invention have been disclosed for illustrative purpose, those skilled in the art will appreciate that various modifications, additions or substitutions are possible, without departing from the scope and spirit of the invention as disclosed in the accompanying claims.

The invention claimed is:

1. A complementary peptide having at least a sequence complementary to a major immunogenic region of an acetylcholine receptor involved in myasthenia gravis, characterized in that the complementary peptide has at least a sequence SEQ. ID. NO:1 with a tryptophan in position 8, said modified tryptophan carrying at least one 2,4,6-trimethoxybenzyl group as hydrocarbonation.

2. A therapeutic composition comprising the complementary peptide according to claim 1 and at least one carrier.

3. A therapeutic composition according to claim 2 comprising from 750 to 25 micrograms of said complementary peptide having at least the sequence SEQ ID NO:1 in 0.5 ml of phosphate buffer saline with at least one adjuvant.

4. A detection kit comprising the complementary peptide according to claim 1 for detecting anti-idiotypic antibodies of the major immunogenic region of myasthenia gravis.

5. A method for manufacturing the complementary peptide according to claim 1, comprising the steps of:

synthesizing of the complementary peptide having at least the sequence SEQ ID NO:1, wherein Xaa at position 8 is a modified tryptophan, purifying the synthesized sequence SEQ ID NO:1 by reverse phase high performance liquid chromatography, hydrocarbonating said tryptophan, in said sequence SEQ ID NO:1 whereby a SEQ ID NO:1 wherein Xaa is said modified tryptophan is obtained, wherein said hydrocarbonation is performed by adding Tmob in order to add at least one 2,4,6-trimethoxybenzyl group to said modified tryptophan.

* * * * *